(12) United States Patent
Gerdes et al.

(10) Patent No.: US 7,189,808 B2
(45) Date of Patent: Mar. 13, 2007

(54) TRANSFER COMPOUNDS, PRODUCTION AND USE THEREOF

(75) Inventors: Johannes Gerdes, Feldhorst (DE); Thomas Scholzen, Neritz (DE); Claudia Wohlenberg, Hamburg (DE)

(73) Assignee: Faustus Forschungs Cie. Translational Cancer Research GmbH, Leipzig (DE)

( * ) Notice: Subject to any disclaimer, the term of this patent is extended or adjusted under 35 U.S.C. 154(b) by 204 days.

(21) Appl. No.: 10/152,212

(22) Filed: May 20, 2002

(65) Prior Publication Data

US 2003/0118600 A1  Jun. 26, 2003

Related U.S. Application Data

(63) Continuation of application No. PCT/EP00/11482, filed on Nov. 17, 2000.

(30) Foreign Application Priority Data

Nov. 18, 1999 (DE) .................. 199 55 576

(51) Int. Cl.
*C07K 14/435* (2006.01)
*A61K 38/17* (2006.01)

(52) U.S. Cl. ...................... 530/350; 530/358
(58) Field of Classification Search ................ 530/350, 530/358
See application file for complete search history.

(56) References Cited

FOREIGN PATENT DOCUMENTS

WO   WO 97/05265   2/1997
WO   WO 99/61607   12/1999

OTHER PUBLICATIONS

MacCallum, D. et al., "The biochemical characterization of the DNA binding activity of pKi67", Jun. 2000, J. Pathol., vol. 191: pp. 286-298.*

Schlüter et al., 1993, *J. Cell Biol.* 123(3): 513-522.

Ducurow, M., Cell Proliferation-Associated Nuclear Antigen Defined by Antibody Ki-67: a New Kind of Cell Cycle-Maintaining Proteins, Archivum Immunologiae et Therapiae Experimentalis, 1994, 43, 117-121.

Gene Expression, Voyager™ Vectors, Invitrogen pamphlet, pp. 104, 105, 109.

Madshus, I., Entry of Diphtheria Toxin-Protein A Chimeras into Cells, The Journal of Biological Chemistry, vol. 266, No. 26, Issue of Sep. 15, 1991, pp. 17446-17453.

Schluter, C., The Cell Proliferation-associated Antigen of Antibody Ki-67: A very Large, Ubiquitous Nuclear Protein with Numerous Repeated Elements, Representing a New Kind of Cell Cycle-maintaining Proteins, The Journal of Cell Biology, vol. 123, No. 3, Nov. 1993, p. 513-522.

Scholzen, C. Evidence for a role of the Ki-67 repeats in guiding the Ki-67 protein to the nucleoli and the perichromosomal layer, (abstract only).

Shayan, P., The proliferation-associated nuclear protein Ki-67 in the bovine system: partial characterization and its application for determination of the proliferation of Theileria-infected bovine cells, Springer-Vertag 1999, pp. 613-620.

Wiedlocha, A., Tight folding of acidic fibroblast growth factor prevents its translocation to the cytosol with diphtheria toxin as vector, The EMBO Journal, vol. 11 No. 13, pp. 4835-4842, 1992.

* cited by examiner

*Primary Examiner*—Scott D. Priebe
*Assistant Examiner*—Michael Burkhart
(74) *Attorney, Agent, or Firm*—Akin Gump Strauss Hauer & Feld, LLP

(57) ABSTRACT

The invention relates to the use of a carboxy-terminal fragment of the Ki-67 protein or of an active part, fragment or homologue thereof as a compound that can be used for intracellular transfer and for the introduction in and the release by the cells. The invention further relates to transfer compounds that contain the above-mentioned Ki-67 protein and to the vectors encoding the same. The invention also relates to corresponding pharmaceutical compositions and to the use of the transfer protein as an excipient or active agent in the treatment of diseases.

5 Claims, 6 Drawing Sheets

```
HindIII    10           20          30 BamHI   40          50          60
AAGCTTGATATCGAATTCCTGCAGCCCGGGGGATCCAGCATTCCGGTACTGTTGGTAAAA 70          80          90         100         110         120
TGGCAAGAGGCAAATCATCCGAACCCGTGGTCATCATGAAGAGAAGTTTGAGGACTTCTG
                                        M   A   R   G   K   S   S   E   P   V   V   I   M   K   R   S   L   R   T   S 130         140         150         160         170         180
CAAAAAGAATTGAACCTGCGGAAGAGCTGAACAGCAACGACATGAAAACCAACAAAGAGG
 A   K   R   I   E   P   A   E   E   L   N   S   N   D   M   K   T   N   K   E 190         200         210         220         230         240
AACACAAATTACAAGACTCGGTCCCTGAAAATAAGGGAATATCCCTGCGCTCCAGACGCC
 E   H   K   L   Q   D   S   V   P   E   N   K   G   I   S   L   R   S   R   R 250         260         270         280         290         300
AAGATAAGACTGAGGCAGAACAGCAAATAACTGAGGTCTTTGTATTAGCAGAAAGAATAG
 Q   D   K   T   E   A   E   Q   Q   I   T   E   V   F   V   L   A   E   R   I 310         320         330         340         350         360
AAATAAACAGAAATGAAAAGAAGCCCATGAAGACCTCCCCAGAGATGGACATTCAGAATC
 E   I   N   R   N   E   K   K   P   M   K   T   S   P   E   M   D   I   Q   N 370         380         390         400         410         420
CAGATGATGGAGCCCGGAAACCCATACCTAGAGACAAAGTCACTGAGAACAAAAGGTGCT
 P   D   D   G   A   R   K   P   I   P   R   D   K   V   T   E   N   K   R   C 430         440         450         460         470         480
TGAGGTCTGCTAGACAGAATGAGAGCTCCCAGCCTAAGGTGGCAGAGGAGAGCGGAGGGC
 L   R   S   A   R   Q   N   E   S   S   Q   P   K   V   A   E   E   S   G   G 490         500         510         520         530         540
AGAAGAGTGCGAAGGTTCTCATGCAGAATCAGAAAGGGAAAGGAGAAGCAGGAAATTCAG
 Q   K   S   A   K   V   L   M   Q   N   Q   K   G   K   G   E   A   G   N   S 550         560         570         580         590         600
ACTCCATGTGCCTGAGATCAAGAAAGACAAAAAGCCAGCCTGCAGCAAGCACTTTGGAGA
 D   S   M   C   L   R   S   R   K   T   K   S   Q   P   A   A   S   T   L   E 610         620         630         640         650         660
GCAAATCTGTGCAGAGAGTAACGCGGAGTGTCAAGAGGTGTGCAGAAAATCCAAAGAAGG
 S   K   S   V   Q   R   V   T   R   S   V   K   R   C   A   E   N   P   K   K 670         680         690         700         710         720
CTGAGGACAATGTGTGTGTCAAGAAAATAAGAACCAGAAGTCATAGGGACAGTGAAGATA
 A   E   D   N   V   C   V   K   K   I   R   T   R   S   H   R   D   S   E   D NotI 733
TTTGAGCGGCCGC
 I   *
```

Fig. 1

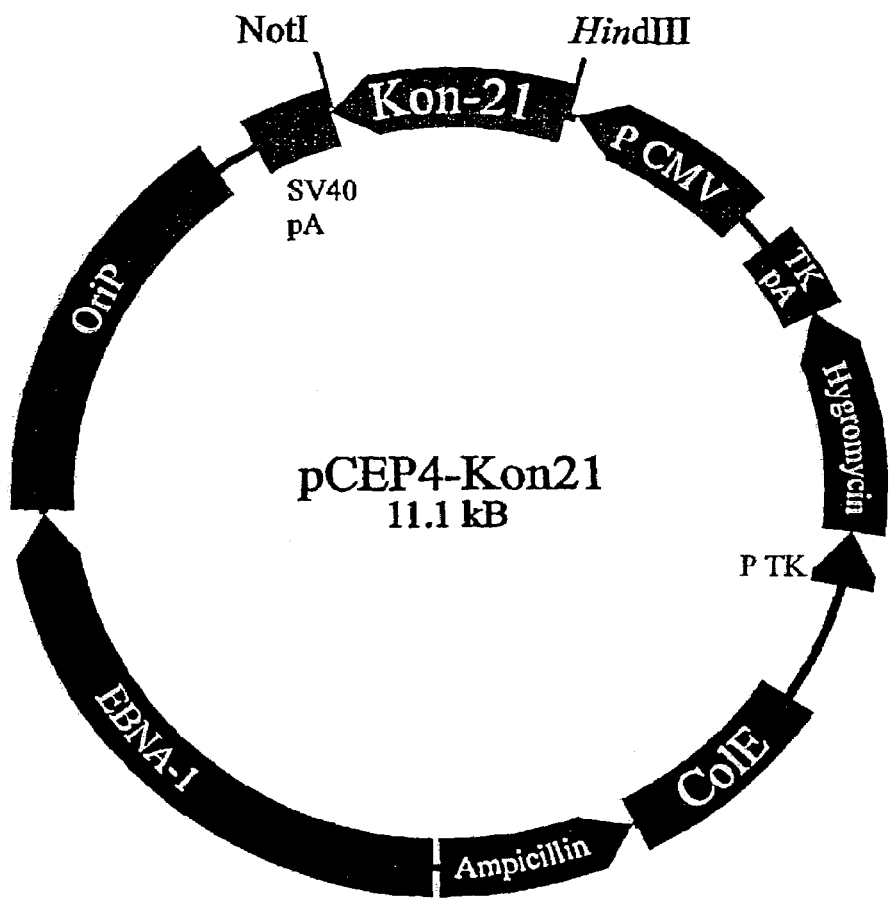
Fig. 2: map of the vector used, pCEP4-Kon21

SEQUENCE LISTING

<160> NUMBER OF SEQ ID NOS: 2

<210> SEQ ID NO 1
<211> LENGTH: 733
<212> TYPE: DNA
<213> ORGANISM: artificial sequence
<220> FEATURE:
<223> OTHER INFORMATION: Kon21-DNA insert sequence
<220> FEATURE:
<221> NAME/KEY: CDS
<222> LOCATION: (60)..(722)
<223> OTHER INFORMATION:

<400> SEQUENCE: 1

```
aagcttgata tcgaattcct gcagcccggg ggatccagca ttccggtact gttggtaaa      59 atg gca aga ggc aaa tca tcc gaa ccc gtg gtc atc atg aag aga agt     107
Met Ala Arg Gly Lys Ser Ser Glu Pro Val Val Ile Met Lys Arg Ser
1               5                   10                  15 ttg agg act tct gca aaa aga att gaa cct gcg gaa gag ctg aac agc     155
Leu Arg Thr Ser Ala Lys Arg Ile Glu Pro Ala Glu Glu Leu Asn Ser
            20                  25                  30 aac gac atg aaa acc aac aaa gag gaa cac aaa tta caa gac tcg gtc     203
Asn Asp Met Lys Thr Asn Lys Glu Glu His Lys Leu Gln Asp Ser Val
        35                  40                  45 cct gaa aat aag gga ata tcc ctg cgc tcc aga cgc caa gat aag act     251
Pro Glu Asn Lys Gly Ile Ser Leu Arg Ser Arg Arg Gln Asp Lys Thr
    50                  55                  60 gag gca gaa cag caa ata act gag gtc ttt gta tta gca gaa aga ata     299
Glu Ala Glu Gln Gln Ile Thr Glu Val Phe Val Leu Ala Glu Arg Ile
65                  70                  75                  80 gaa ata aac aga aat gaa aag aag ccc atg aag acc tcc cca gag atg     347
Glu Ile Asn Arg Asn Glu Lys Lys Pro Met Lys Thr Ser Pro Glu Met
                85                  90                  95 gac att cag aat cca gat gat gga gcc cgg aaa ccc ata cct aga gac     395
Asp Ile Gln Asn Pro Asp Asp Gly Ala Arg Lys Pro Ile Pro Arg Asp
            100                 105                 110 aaa gtc act gag aac aaa agg tgc ttg agg tct gct aga cag aat gag     443
Lys Val Thr Glu Asn Lys Arg Cys Leu Arg Ser Ala Arg Gln Asn Glu
        115                 120                 125 agc tcc cag cct aag gtg gca gag gag agc gga ggg cag aag agt gcg     491
Ser Ser Gln Pro Lys Val Ala Glu Glu Ser Gly Gly Gln Lys Ser Ala
    130                 135                 140 aag gtt ctc atg cag aat cag aaa ggg aaa gga gaa gca gga aat tca     539
Lys Val Leu Met Gln Asn Gln Lys Gly Lys Gly Glu Ala Gly Asn Ser
145                 150                 155                 160 gac tcc atg tgc ctg aga tca aga aag aca aaa agc cag cct gca gca     587
Asp Ser Met Cys Leu Arg Ser Arg Lys Thr Lys Ser Gln Pro Ala Ala
                165                 170                 175 agc act ttg gag agc aaa tct gtg cag aga gta acg cgg agt gtc aag     635
Ser Thr Leu Glu Ser Lys Ser Val Gln Arg Val Thr Arg Ser Val Lys
            180                 185                 190 agg tgt gca gaa aat cca aag aag gct gag gac aat gtg tgt gtc aag     683
Arg Cys Ala Glu Asn Pro Lys Lys Ala Glu Asp Asn Val Cys Val Lys
        195                 200                 205 aaa ata aga acc aga agt cat agg gac agt gaa gat att tgagcggccg c    733
Lys Ile Arg Thr Arg Ser His Arg Asp Ser Glu Asp Ile
    210                 215                 220
```

<210> SEQ ID NO 2
<211> LENGTH: 221

```
<212> TYPE: PRT
<213> ORGANISM: artificial sequence
<220> FEATURE:
<223> OTHER INFORMATION: Kon21-DNA insert sequence

<400> SEQUENCE: 2

Met Ala Arg Gly Lys Ser Ser Glu Pro Val Ile Met Lys Arg Ser
1               5                   10                  15

Leu Arg Thr Ser Ala Lys Arg Ile Glu Pro Ala Glu Glu Leu Asn Ser
            20                  25                  30

Asn Asp Met Lys Thr Asn Lys Glu Glu His Lys Leu Gln Asp Ser Val
            35                  40                  45

Pro Glu Asn Lys Gly Ile Ser Leu Arg Ser Arg Arg Gln Asp Lys Thr
            50                  55                  60

Glu Ala Glu Gln Gln Ile Thr Glu Val Phe Val Leu Ala Glu Arg Ile
65                  70                  75                  80

Glu Ile Asn Arg Asn Glu Lys Lys Pro Met Lys Thr Ser Pro Glu Met
                85                  90                  95

Asp Ile Gln Asn Pro Asp Asp Gly Ala Arg Lys Pro Ile Pro Arg Asp
                100                 105                 110

Lys Val Thr Glu Asn Lys Arg Cys Leu Arg Ser Ala Arg Gln Asn Glu
            115                 120                 125

Ser Ser Gln Pro Lys Val Ala Glu Glu Ser Gly Gly Gln Lys Ser Ala
            130                 135                 140

Lys Val Leu Met Gln Asn Gln Lys Gly Lys Gly Glu Ala Gly Asn Ser
145                 150                 155                 160

Asp Ser Met Cys Leu Arg Ser Arg Lys Thr Lys Ser Gln Pro Ala Ala
                165                 170                 175

Ser Thr Leu Glu Ser Lys Ser Val Gln Arg Val Thr Arg Ser Val Lys
                180                 185                 190

Arg Cys Ala Glu Asn Pro Lys Lys Ala Glu Asp Asn Val Cys Val Lys
                195                 200                 205

Lys Ile Arg Thr Arg Ser His Arg Asp Ser Glu Asp Ile
    210                 215                 220
```

TRANSFER COMPOUNDS, PRODUCTION AND USE THEREOF

CROSS-REFERENCE TO RELATED APPLICATIONS

This application is a continuation of International Patent Application No. PCT/EP00/11482, filed Nov. 17, 2000, published as WO 01/36629 on May, 25, 2001, the disclosure of which is incorporated herein by reference.

BACKGROUND OF THE INVENTION

The present invention relates to compounds which are capable of introducing associated compounds into a cell. In particular, the present invention relates to a transfer compound which comprises the carboxy-terminal fragment of the Ki-67 protein. Furthermore, this application encompasses vectors which contain the sequence coding for the transfer compound, transfer compounds and pharmaceutical compositions containing said transfer compounds and/or vectors. Claimed are also methods for the production thereof as well as the use of said transfer compounds. Corresponding methods for the treatment or prevention of diseases by gene therapy with the aid of said transfer compounds are within the scope of the invention.

Protein targeting is a biological process of fundamental importance which is controlled by highly coordinated mechanisms.

Thus protein export or secretion occurs via specific reaction routes for which characterized signal sequences are used for directing the proteins into the subcellular compartments involved, e.g. endoplasmic reticulum, Golgi complex and vesicles. Signal sequences are also used for the intracellular transfer. For instance, nuclear localization sequences (NLS) have been described for the transfer of proteins into the cell nucleus; these nuclear localization sequences direct large proteins, which cannot pass into the nucleus by diffusion, through the nuclear pores into the cell nucleus.

The uptake of proteins in a cell is also regulated in a complex manner. One example to be given here is the receptor-mediated endocytosis which serves the import of specific proteins by binding to receptors on the cell membrane and subsequent inclusion in vesicles. This process serves, on the one hand, to supply cells with metabolites required for metabolism and, on the other hand, to degrade proteins. Furthermore, the receptor-mediated endocytosis mediates the cellular responses to many mediators, such as peptide hormones or growth factors. Finally, said process is used by viruses and toxins to pass into cells.

It is desired for many applications in biomedical research, diagnostics and therapy to introduce substances, preferably proteins, nucleic acids, non-peptide molecules, such as oligosaccharides, lipids or drugs or marker molecules, into cells. Since many of the aforementioned substances are not able to pass through the cell membrane, different methods are employed for the introduction of said substances and their intracellular production, respectively.

Apart from mechanical methods, such as e.g. microinjection, the person skilled in the art is well aware of e.g. expression techniques used in molecular biology for this purpose. The last-mentioned methods, however, are not very efficient; as a rule, an expression is only successful in 2–20% of the cells, which renders e.g. an in-vivo application very difficult. This drawback was recently overcome by using a structural protein (VP22) of the herpes simplex virus type 1 (HSV-1). After classic transfection with expression vectors it was found that, in contrast to another HSV-1 protein which (as expected) could only be detected in 2–5% of the cells, the VP22 could be detected in 100% of the cells (PCT application no. WO 97/05265). Furthermore it was found that said viral protein as a fusion protein can introduce various polypeptides into target-cell populations (WO 97/05265). However, it is well known to the person skilled in the art that viral proteins can initiate pleiotropic effects preferably in mammalian cells, cell assemblies and the whole organism, respectively.

For instance, the E1A protein of adenoviruses as well as the T antigen of the simian virus 40 (SV40) start a multitude of processes in the cells. These include, for instance, initiation of the DNA synthesis as well as the activation of various enzymes, such as dihydrofolate reductase, thymidine kinase and DNA polymerase (Nevins, J. R. Adenovirus E1A: Transcription regulation and alteration of cell growth control, in Doerfler, W. and Böhm, P., The molecular repertoire of Adenovirus III: Biology and pathogenesis, Springer Verlag Berlin, Heidelberg, N.Y., 1995). A further example are the pleiotropic properties of the structural proteins of reoviruses (Yue, Z. and Shatkin, A. J., Enzymatic and control functions of Reovirus structural proteins, in Tyler, K. L. and Oldstone, M. B. A., Reoviruses I: Structure, Proteins, and Genetics, Springer Verlag Berlin, Heidelberg, N.Y., 1998).

It is therefore the object of the present invention to provide a transfer vehicle for compounds to overcome such drawbacks. The transfer compounds can be used in gene therapy.

The transfer vehicle according to the invention is from a mammal, preferably of human origin.

BRIEF SUMMARY OF THE INVENTION

The present object is achieved according to the invention by a carboxy-terminal fragment of the human Ki-67 protein. The invention includes a method of transferring a compound into a cell using the carboxy-terminal fragment. The method comprising associating the compound with a carrier selected from the group consisting of i) a carboxy-terminal fragment of Ki-67 protein, ii) an active part of the fragment, iii) a portion of the fragment, and iv) a homologue of the fragment and contacting the cell with the carrier-associated compound.

A further aspect of the present invention relates to a vector coding for said fragment.

Described is further a transfer protein which comprises the carboxy-terminal fragment of the Ki-67 protein. The transfer protein can, for example, comprise one of i) a carboxy-terminal fragment of the Ki-67 protein, ii) an active part of the fragment, iii) a portion of the fragment, and iv) a homologue of the fragment. However, the transfer protein is not the full-length Ki-67 protein. The transfer protein can be used for treatment, prevention, or therapy of a disease by contacting cells of a patient with the transfer protein having a pharmaceutically active agent associated therewith. The agent is transferred into the cells and the disease is treated, prevented, or alleviated.

The transfer protein according to the invention may here be the carboxy-terminal fragment of the Ki-67 protein of man, mouse, rat or of another species.

Furthermore, the invention relates to methods for producing transfer compounds and for producing vectors coding for said transfer compounds.

A further aspect is a method for transferring compounds into a target group selected from cell lines, cells in vitro, tumor cells, tissue, etc., with the help of the above-mentioned transfer protein according to the invention or of a vector containing the sequence coding for a transfer protein according to the invention. In one embodiment, a compound to a second cell by a) introducing the expression vector encoding a transfer protein having the compound linked thereto described herein into a first cell, b) expressing the vector in the first cell, whereby the transfer protein having the compound linked thereto is excreted, and c) contacting the excreted protein with the second cell.

Furthermore, the present invention includes the use of the above-mentioned compounds for the transfer of associated compounds, and methods for the treatment and prevention of diseases, in particular the use in gene therapy.

Also provided is a pharmaceutical composition containing the transfer protein of the invention alone or associated with a further compound, as well as a method for the production thereof.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 1 is a Representation of the nucleotide sequence (SEQ ID NO: 1) of the Kon21-DNA insert. The numbering of the base pairs as well as the restriction sites used for cloning are indicated above the nucleotide sequence. The amino acid sequence (SEQ ID NO: 2) of the derived Kon21 protein is shown below the nucleotide sequence. Nucleotides shown in bold face are part of the restriction sites used. Underlined nucleotides have been introduced into the construct by the deoxyoligonucleotide primers used. For a better survey only one of the two DNA strands has been indicated in 5'-3' direction.

FIG. 2: Map of the vector used, pCEP4-Kon21.

DETAILED DESCRIPTION OF THE INVENTION

The fragment according to the invention, namely the carboxy-terminal region of the Ki-67 protein, comprises the region of the amino acids from 3037 to 3256 of the Ki-67 protein, as deposited in Swiss Prot under Accession No. P46013, or fragments of the region, as exist due to natural variation of the genome. Moreover, the fragment may only comprise parts of the above-mentioned fragment or homologues thereof as long as the function as a transfer protein is maintained.

Homologue means in this instance that there is at least a homology of 80% in the amino acid residues which are essential for the function of the carboxy-terminal region as a transfer compound.

The human Ki-67 protein is expressed in all nuclei of proliferating cells in all active phases of the cell cycle, i.e. in G1, S, G2 and mitosis, but not in quiescent G0 cells (Gerdes et al. Cell cycle analysis of a cell proliferation-associated human nuclear antigen defined by the monoclonal antibody Ki-67 J. Immunol. 133:1710–15, 1984). The cDNA of the human Ki-67 and of the murine equivalent are known and show no significant homologies to other proteins (Schlüter et al. The cell proliferation-associated antigen of antibody Ki-67: a very large, ubiquitous nuclear protein with numerous repeated elements, representing a new kind of cell cycle-maintaining proteins J. Cell Biol. 123:513–522, 1993, Starborg et al. The murine Ki-67 cell proliferation antigen accumulates in the nucleolar and heterochromatic regions of interphase cells and at the periphery of the mitotic chromosomes in a process essential for cell cycle progression J. Cell Sci. 109:143–153, 1996). The human Ki-67 protein has several NLS and can physiologically be detected only in the cell nucleus, except during mitosis. It could only be demonstrated after microinjection of antibodies that the Ki-67 protein is formed in the cytoplasm and is transferred very rapidly, presumably in supramolecular complexes, into the cell nucleus (Heyden et al. Cytoplasmic observation of the Ki-67 protein and immunofluorescence staining of its transport to the nucleus Eur. J. Cell Biol. Vol 42: 33, 1996). So far a transfer out of the nucleus or even out of the cell has not been observed or described. Therefore, the finding we made when examining the function of partial structures of the Ki-67 protein has been all the more surprising.

Figure 3:
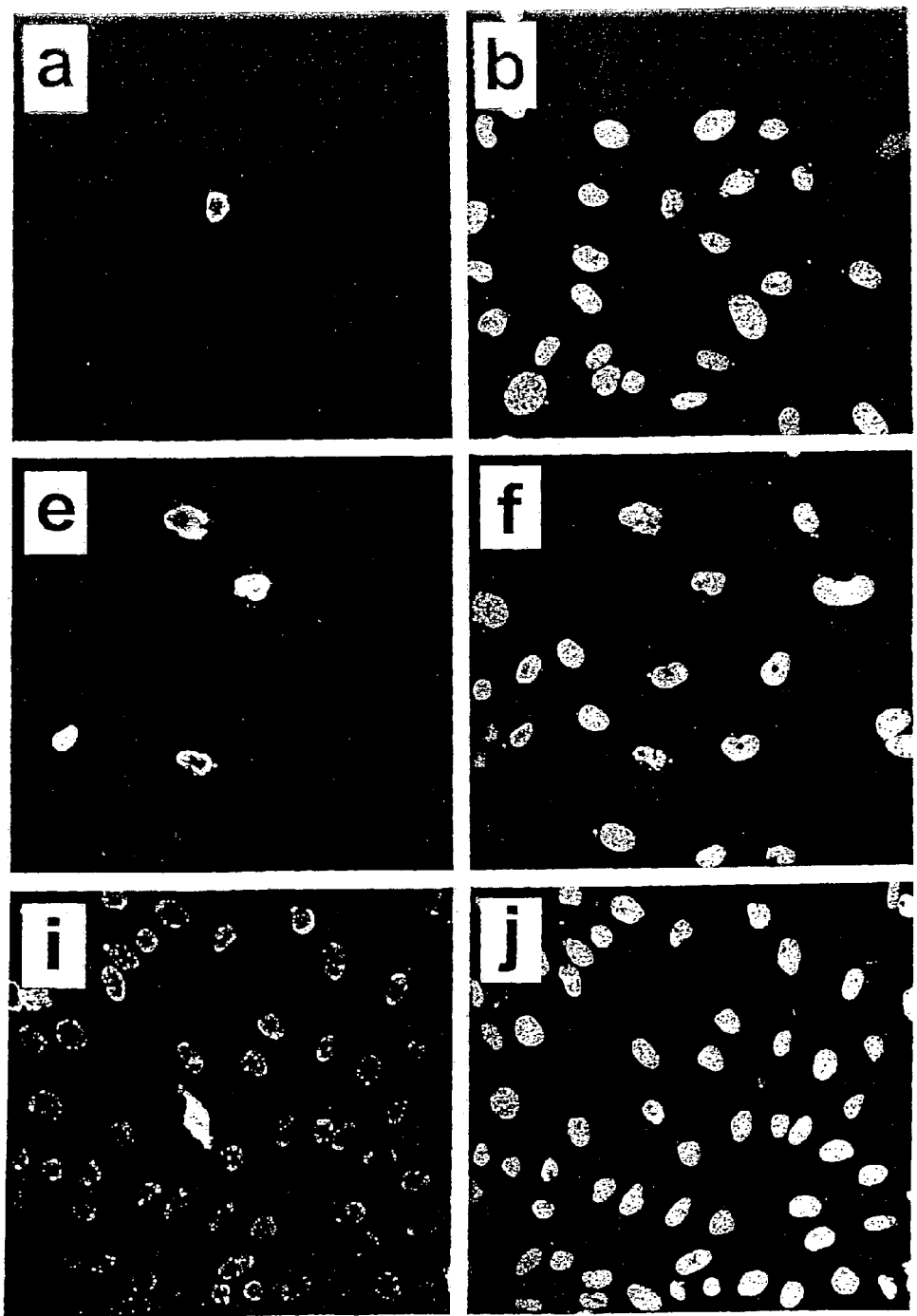
FIG. 3: Micrographs of cells 6 hours (FIG. 3a–FIG. 3d), 10 hours (FIG. 3e–FIG. 3h), and 24 hours (FIG. 3i–FIG. 3l) after transfection; test conditions, see Example 1. Staining with MIB-21 (FIG. 3a, FIG. 3e, FIG. 3i, FIG. 3c, FIG. 3g, FIG. 3k) and counterstaining with propidium iodide (FIG. 3b, FIG. 3f, FIG. 3j, FIG. 3d, FIG. 3h, FIG. 3l). The cells in the left half of the picture were transfected with pCEP4-Kon21 (FIG. 3a, FIG. 3b, FIG. 3e, FIG. 3f, FIG. 3i, FIG. 3j) and the cells in the right half with pCEP4 (FIG. 3c, FIG. 3d, FIG. 3g, FIG. 3h, FIG. 3k, FIG. 3l).
Figure 3:
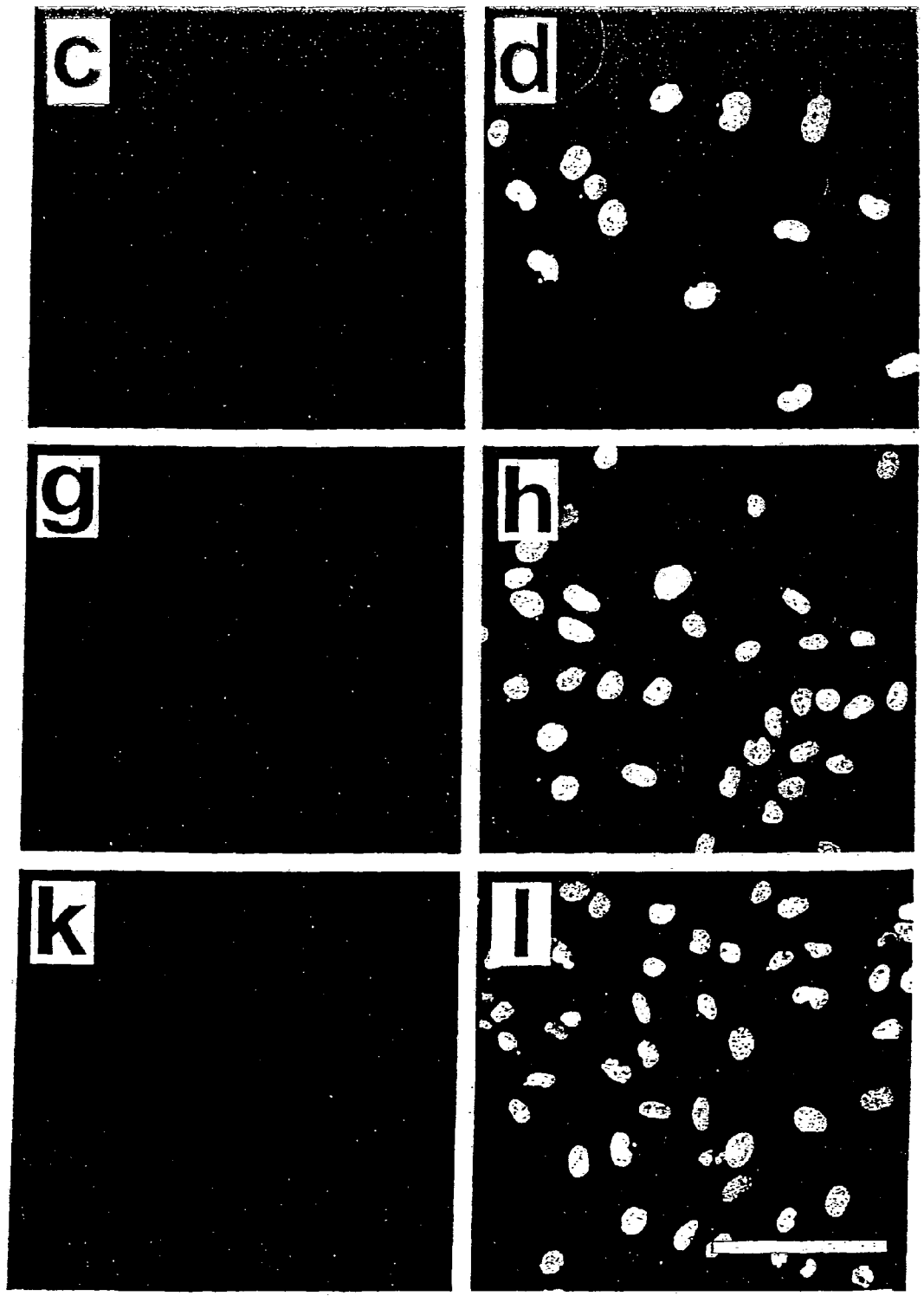

A carboxy-terminal fragment of the human Ki-67 protein transiently expressed in CHO-K1 (Chinese hamster ovary-K1, ATTC No. CRL 9618) cell line cells, which is called KON-21 (FIG. 1), showed an entirely unexpected immunocytologic distribution pattern of the polypeptide produced. As expected, in 5–20% of the cells the KON-21 was expressed strongly cytoplasmically, like in control proteins. Moreover, the KON-21 could also be detected in 100% of the cell nuclei. It could be demonstrated that the Kon-21 peptide is first produced in 5–20% of the cells in cytoplasm and, since it contains an NLS, is rapidly transferred into the cell nucleus of such producer cells (Example 1 and FIG. 3). Moreover, the KON-21 is passed on to neighboring non-transfected cells and localized in said recipient cells in the cell nucleus. This intercellular transfer of the KON-21 does probably not follow any of the above-described conventional protein export or import pathways because the KON-21 is devoid of classic signal sequences for such processes. The intracellular transfer into the cell nuclei is probably achieved via the Ran-GTP-importin-alpha system (Goerlich D. Transport into and out of the cell nucleus EMBO J. Vol. 17: 2721–27 1998) with the help of the NLS of the KON-21.

Experiments with constructs coding for a fusion protein with the KON-21 protein showed that said fusion proteins are efficiently expressed and intercellularly transferred.

Figure 4:
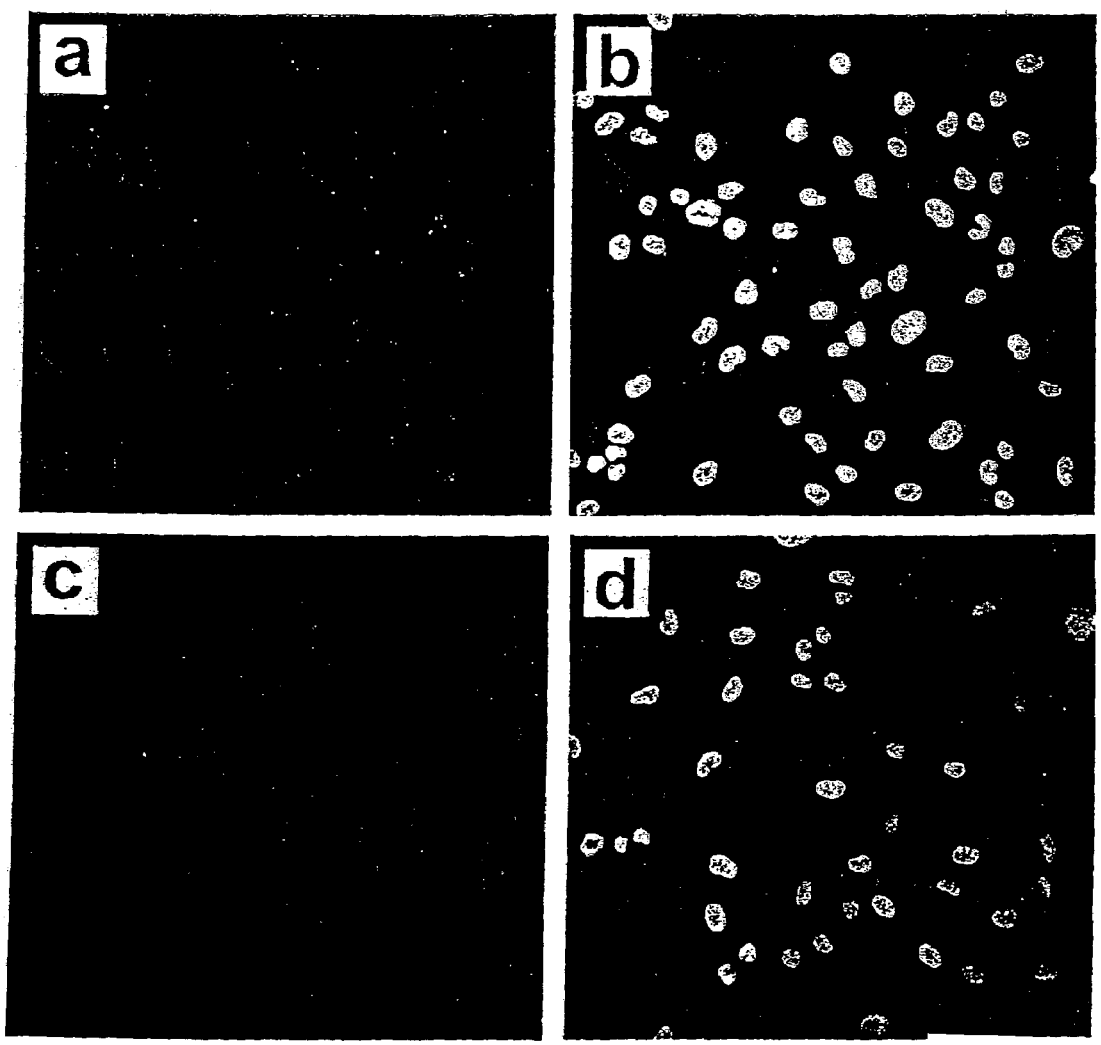
FIG. 4: Micrographs of cells 5 minutes (FIG. 4a–FIG. 4d) and 1 hour (FIG. 4e–FIG. 4h) after addition of high salt lysate, see Example 2. The cells in the left half of the picture were stained with MIB-21 (FIG. 4a, FIG. 4c, FIG. 4e, FIG. 4g). The right half of the picture shows the same cells counterstained with propidium iodide (FIG. 4b, FIG. 4d, FIG. 4f, FIG. 4h). The upper half of the picture shows the cells after 5 minutes (FIG. 4a–FIG. 4d), the lower half shows cells after incubation for 1 hour with the high salt lysate (FIG. 4e–FIG. 4h). Cells after addition of high salt lysate from pCEP4-Kon21 transfected cells (FIG. 4a, FIG. 4b, FIG. 4e, FIG. 4f) and high salt lysate from pCEP4-transfected cells (FIG. 4c, FIG. 4d, FIG. 4g, FIG. 4h).
Figure 4:
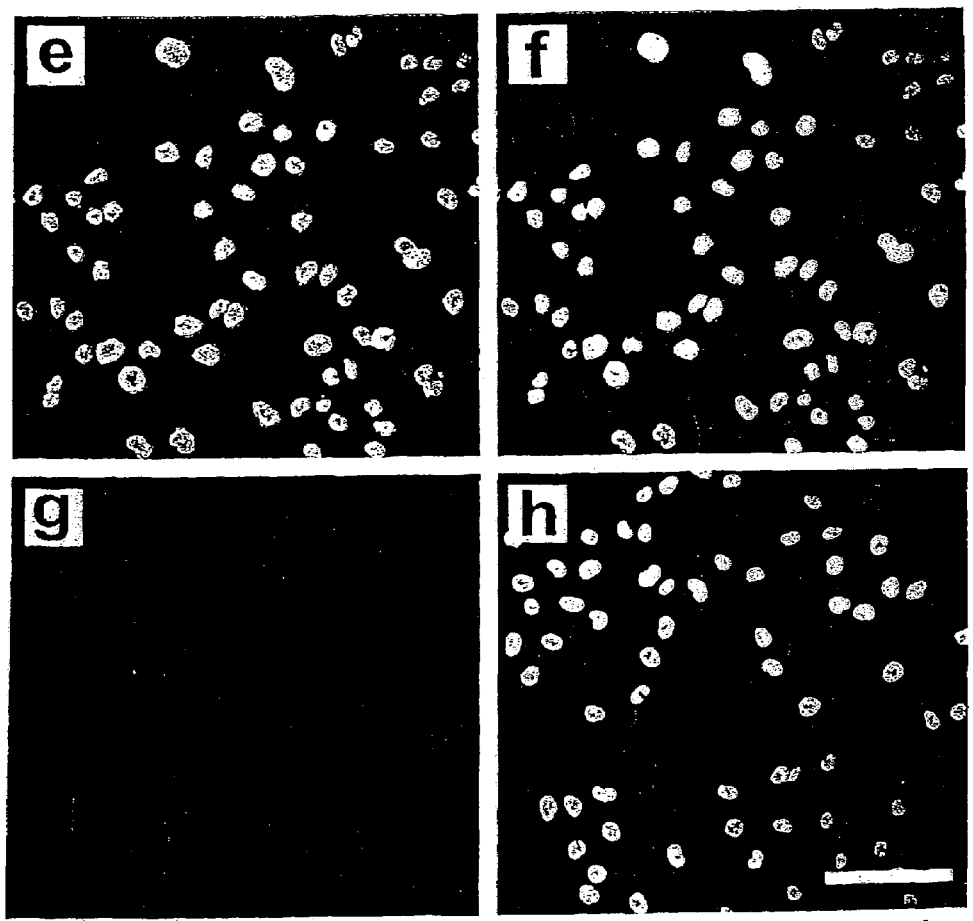

In experiments in which the KON-21 in cell extracts was added to the culture medium of target cells, the KON-21 alone or in combination with a fusion protein was transferred in a highly efficient and very rapid way into the target cells (Example 2 and FIG. 4). This aspect further permits the transfer of non-peptidyl substances which cannot be expressed intracellularly.

These above-mentioned aspects permit the use of said transfer compounds in gene therapy for diseases, such as cancer, allergy, autoimmune diseases, etc. This means that the invention also includes methods for treating and as well as for preventing, diseases.

The Kon21-DNA construct was prepared with the help of standard techniques used in molecular biology. To this end cDNA of the cell line HeLa S3 was amplified by means of PCR. The restriction sites for the subsequent cloning into a plasmid vector, as well as the sequence motifs required for an efficient translation of the mRNA, were introduced by using deoxyoligonucleotide primers which carried additional nucleotide sequences at their 5' ends (see FIG. 1). The Kon21-DNA construct was first cloned into the cloning vector pBluescript SK of the company Stratagene (La Jolla, Calif., USA). Sequencing of the insert DNA yielded two deviations from the already published DNA sequence of the Ki-67 cDNA (Schlüter et al. supra). The sequence analysis of several independent clones confirmed the correctness of the sequences obtained. For the expression the insert DNA was cut by means of the restriction enzyme HindIII and NotI from the cloning vector and cloned into the eukaryotic expression vector pCEP4 of Invitrogen Corporation (Carlsbad, Calif., USA). FIG. 1 shows the complete nucleotide sequence of the DNA insert and the amino acid sequence of the expression product coded therefrom. FIG. 2 schematically shows the structure of the Kon21 expression construct.

EXAMPLES

Example 1

After transfection the KON-21 protein is transported to all cells of a culture.

CHO cells were transiently transfected with the construct pCEP4-Kon21 and analyzed at different times. To this end the slides with the cells grown thereon were rinsed in PBS/10% FCS, air-dried for about 6 hours and then fixed in chloroform/acetone. This process was followed by immunofluorescence staining with the monoclonal antibody MIB-21, which specifically recognizes the KON-21 protein. The binding of the antibody MIB-21 was then detected by means of an Alexa488-conjugated goat anti-mouse antibody (Molecular Probes Inc., Eugene, Oreg., USA). For better orientation the DNA of the cells was additionally counterstained with propidium iodide. For control of the staining CHO cells were also transfected with the expression vector pCEP4. Micrographs of cells 6 hours (FIG. 3a–FIG. 3d), 10 hours (FIG. 3e–FIG. 3h), and 24 hours (FIG. 3i–FIG. 3l) after transfection. Staining was performed with MIB-21 (FIG. 3a, FIG. 3e, FIG. 3i, FIG. 3c, FIG. 3g, FIG. 3k) and counterstaining with propidium iodide (FIG. 3b, FIG. 3f, FIG. 3j, FIG. 3d, FIG. 3h, FIG. 3l). The cells in the left half of the picture were transfected with pCEP4-Kon21 (FIG. 3a, FIG. 3b, FIG. 3e, FIG. 3f, FIG. 3i, FIG. 3j) and the cells in the right half with pCEP4 (FIG. 3c, FIG. 3d, FIG. 3g, FIG. 3h, FIG. 3k, FIG. 3l). While after 6 hours only a few nuclei of pCEP4-Kon21 transfected cells showed some staining with MIB-21, the staining increased after 10 hours, and after 24 hours all of the cell nuclei were stained with MIB-21. By contrast, cells which were transfected with pCEP4 for control purposes only showed a very weak unspecific background staining during the whole period.

Example 2

After addition into the culture medium the KON-21 protein is taken up by all cells of a culture.

About 500,000 CHO cells were transiently transfected with the construct pCEP4-Kon21. For control purposes 500,000 CHO cells were also transfected with the expression vector pCEP4. After incubation in an incubator for 24 hours the cells were harvested and sedimented, and the cell sediment was frozen at −70° C. After thawing the cell sediment was resuspended in 500 µl ice-cold high salt buffer (10 mM HEPES, pH 7.9, 400 mM NaCl, 0.1 mM EDTA, 0.5 mM DTT, 5% glycerol) and sedimented again after incubation at 0° C. for 5 minutes. The supernatant was added to CHO cells in 15 ml culture medium and the cells were analyzed at different times. To this end the slides with the cells grown thereon were rinsed in PBS/10% FCS, air-dried for about 6 hours and then fixed in chloroform/acetone. This process was followed by immunofluorescence staining with the monoclonal antibody MIB-21, which specifically recognizes the KON-21 protein. The binding of the antibody MIB-21 was then detected by means of an Alexa488-conjugated goat anti-mouse antibody (Molecular Probes Inc., Eugene, Oreg., USA). For better orientation the DNA of the cells was additionally counterstained with propidium iodide. Micrographs of cells 5 minutes (FIG. 4a–FIG. 4d) and 1 hour (FIG. 4e–FIG. 4h) after addition of the high salt lysate. The cells in the left half of the picture were stained with MIB-21 (FIG. 4a, FIG. 4c, FIG. 4e., FIG. 4g). The right half of the picture shows the same cells counterstained with propidium iodide (FIG. 4b, FIG. 4d, FIG. 4f, FIG. 4h). The upper half of the picture shows cells after 5 minutes (FIG. 4a–FIG. 4d), the lower half shows cells after incubation with the high salt lysate for 1 hour (FIG. 4e–FIG. 4h). Cells after addition of high salt lysate from pCEP4-Kon21 transfected cells (FIG. 4a, FIG. 4b, FIG. 4e, FIG. 4f) and high salt lysate from pCEP4 transfected cells (FIG. 4c, FIG. 4d, FIG. 4g, FIG. 4h), respectively. After addition of high salt lysate from pCEP4-Kon21 transfected cells, a weak staining of the cell nuclei with MIB-21 was already detected after 5 minutes. After one hour all of the cell nuclei show a strong staining with MIB-21. By contrast, cells which were incubated with high salt lysate from pCEP4 transfected cells show only a very weak unspecific background staining.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An isolated transfer protein comprising fragment Kon-21 of the Ki-67 protein, the fragment having the amino acid sequence set forth in SEQ ID NO:2.

2. The transfer protein of claim 1, further comprising a compound linked thereto.

3. The transfer protein of claim 2, wherein the compound comprises a polypeptide.

4. The transfer protein of claim 1, wherein the transfer protein is produced in a recombinant manner.

5. The transfer protein of claim 2, wherein the compound is a non-peptidyl substance.

* * * * *